United States Patent [19]
Pine et al.

[11] Patent Number: 5,932,206
[45] Date of Patent: Aug. 3, 1999

[54] OPHTHALMIC DRUG DISPENSING SYSTEM

[76] Inventors: Jerrold S. Pine, 9555 Saddlebrook Dr., Boca Raton, Fla. 33496; Joel Nathan, 7525 NW. 65th La., Parkland, Fla. 33067

[21] Appl. No.: 08/962,557

[22] Filed: Oct. 31, 1997

[51] Int. Cl.[6] ............ A61M 35/00; A61K 31/74
[52] U.S. Cl. .................... 424/78.04; 604/295
[58] Field of Search .............. 604/295; 424/78.04

[56] References Cited

U.S. PATENT DOCUMENTS

| | | | |
|---|---|---|---|
| 4,909,801 | 3/1990 | Casey | 604/306 |
| 5,366,448 | 11/1994 | Besilice | 604/290 |
| 5,373,964 | 12/1994 | Moore | 222/1 |
| 5,558,653 | 9/1996 | Lindstrom | 604/295 |
| 5,584,823 | 12/1996 | Valberg | 604/294 |

*Primary Examiner*—Carlos A. Azpuru
*Attorney, Agent, or Firm*—Oltman, Flynn & Kubler

[57] ABSTRACT

This invention pertains to an apparatus for a drug delivery system to administer topical ophthalmic drug preparations. The apparatus relates to an optical gauging assembly which, when combined with or coupled to any standard topical ophthalmic drug dispensing unit, enables the user to view a target, visually align the dispenser tip, and administer an eye drop with precision. There is also a visual mechanism by which the dispenser tip is prevented from gaining too close proximity and contacting the eye, thus preventing contamination of the medication and its dispenser.

11 Claims, 8 Drawing Sheets

OPHTHALMIC DRUG DISPENSING SYSTEM

BACKGROUND OF THE INVENTION

This invention pertains to a delivery system for administering topical ophthalmic drug preparations, enabling the patient to direct an eye drop into the eye with the ease and accuracy previously only attained by a proficient few. In addition, this particular device may serve to prevent cross-contamination, and ultimately save both the patient and the healthcare system money typically lost to waste.

More specifically, this invention relates to a lens and target system which, when combined with or coupled to any standard topical ophthalmic drug dispensing unit, enables the user to view the target, align the dispenser tip, and administer an eye drop with precision not attained before. To achieve this precision, the target and lens system is calibrated to align with the axis of the eye at a specified distance. The nozzle of the dispenser is aligned adjacent to the target creating the appropriate geometry between the path a dispensed drop of ophthalmic drug takes and the eye. Prior art such as U.S. Pat. No. 5,558,653 "Targeted eye drop dispenser" which uses visual feedback to align an ophthalmic drug dispenser simply helps place the nozzle along the axis of the eye at an arbitary distance selected at random by the user. This is only effective if the axis of the eye and the path a dispensed drop falls are the same. The axis and path are only identical when the eye is rotated 90 degrees with respect to the horizon which can only be easily achieved lying down. Most users dispense eyedrops while standing or sitting with the eye rotated about 50 degrees back and will miss often with those types of implementations.

To efficiently dispense drugs with this invention, the user would tilt his/her head back, position the lens proximal to the eye where drug dispense is desired, align a target with his/her eye until a specified image appears thereby gauging distance, orientation and concentricity with the axis of the eye, and dispense a drop directly into the eye. Since the success rate of delivering a single drop in the desired location, i.e. the eye, will exceed 99%, the amount of waste can be reduced dramaticaly. At the same time, a visual mechanism by which the dispenser tip is prevented from gaining too close proximity and contacting the eye is provided, thus preventing contamination of the medication and its dispenser.

For years, the primary method of medically treating disorders of the eye has been via topical administration of various medications and other chemical compounds useful in combating a host of ophthalmic ailments. In fact, studies show that when measuring concentrations of these compounds at the desired target site (whether it be in the tearfilm, intracorneal, or intraocular), topical delivery equals or exceeds those concentrations obtained by systemic routes (oral or intravenous), and has far fewer systemic untoward signs and symptoms (side effects). Thus, it is no wonder that most remedies and medications are delivered via the topical route. Historically, this has been achieved via ointments, suspensions, solutions, contact lenses, collagen shields, and palpebral inserts. Far and away, the most common mode of delivery has been via topical suspensions and solutions. Typically, dispensers have fairly standard sizes and shapes (although there is some slight variation), and there is a reproducible standard drop size that is governed by the dropper (dispenser) tip. As simple as topical delivery may seem to achieve, there are various difficulties and shortcomings with current topical dispensing units (vials and bottles), many of which have not been previously or adequately addressed and solved.

The most common problem that the typical patient experiences when attempting to use an eyedrop is the inability to introduce a drop into the eye, or simply missing the eye. There are several reasons for this. First, the normal bottle tip is not clearly visible as it approaches a normal emmetropic, hyperopic, or even myopic eye. This immediately leads to the probability that the first drop will become the "test drop", landing on the cheek, forehead, or eyelashes, leading to waste and frustration. Second, there is a natural aversion to a closely approaching objects, causing the eye to wander or drift, and look everywhere but at the dispenser tip. Again, this leads to the possibility that a drop will miss. Finally, most users are not taught how to use eye drops. They are simply given the bottle and instructed to "place one drop in the eye".

The next important issue is one of waste. When a typical eye drop is introduced into the eye, the average inferior cul-de-sac only holds one-quarter to one-half of a standard drop. The remainder is either washed out down the cheek, or drained by the lacrimal system. Large strides in preventing waste were made when a dispenser tip was developed that delivered smaller drop sizes, thus eliminating a portion of waste. However, this advantage is negated if it takes several drops to gain access to the ocular surface. This issue is critical when evaluating cost to) the patient and the healthcare system. The cost problem for the patient is obvious the more drops they use, the greater the amount of money spent. With respect to the healthcare system as a whole, cutting costs are of paramount importance. In fact, many Health Maintenance Organizations (HMO's) will not let their members get refills on their ophthalmic medications more than once a month. The rationale behind this is simple. If the bottle has "x" number of drops in it, it should last "y" number of days. If the patient is not proficient with a high success ratio, then the drops will run out before the specified time allowed. This, in turn, leads to the patient either being without their valuable medications, or having to pay for the medications themselves.

Finally, there is the problem of contamination of the dispenser tip, and cross-contamination between patients. Since the tip is not clearly visible upon the approach to the ocular surface, it oftentimes will inadvertently come in contact with the eye of lid structures. This will lead to an inoculation of the tip with ocular flora, and be a potential source for spreading infection. Although sharing medications in general, especially eye drops, is always discouraged, many different people whether friends or family members, often find the ease and convenience of sharing overwhelmingly tempting. Again, this can lead to cross-contamination and, in turn, spread of infection.

This invention addresses these main issues, and solves the problems at hand. Using the lens and target system, the user is provided with a reproducible method of dispensing eye drops. If the dispenser is too far from the eye or not properly aligned on its axis, the target is not fully visible. If it is too close, another target segment becomes evident, indicating that the tip is indeed too close. When the target is appropriately visualized, the probability that the drop will enter the eye will exceed 99 percent providing that the user does not blink or uses their other hand to hold their eyelids open. If the user is able to attain this high success rate in a reproducible fashion, all of the aforementioned problems are addressed and solved: the drop is easily administered, there is a significant reduction is waste, and the chance of contamination is diminished dramatically.

Most of the current problems of efficiently dispensing ophthalmic drugs stem from user error. Therefore, it is the goal of this device to create a "user friendly" ophthalmic drug dispenser.

SUMMARY OF THE INVENTION

It is therefore an object of this invention to provide visual feedback from a calibrated optical gauging system to properly align in ophthalmic drug dispenser to dispense drugs into an eye with a high rate of accuracy.

It is another object of this invention to provide visual feedback from a calibrated optical gauging system when the ophthalmic drug dispenser becomes too close to the users eye to prevent eye contact and subsequent contamination.

BRIEF DESCRIPTION OF THE DRAWINGS

The present invention will become more fully understood from the detailed description given hereinbelow and the accompanying drawings which are given by way of illustration only, and thus are not limitive of the present invention, and wherein:

FIGS. 3A, 3B, 3C, 3D, 3E and 3F are partial cross-sectional views of an optical gauging assembly, while it is in use, according to the invention.

DETAILED DESCRIPTION OF THE PREFERRED EMBODIMENTS

Figure 1A:
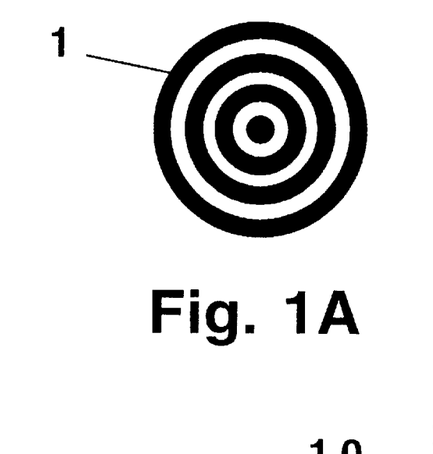
FIGS. 1A, 1B, 1C, and 1D are partial cross-sectional views of an optical gauging assembly, while it is in use, according to the invention.
Figure 1B:
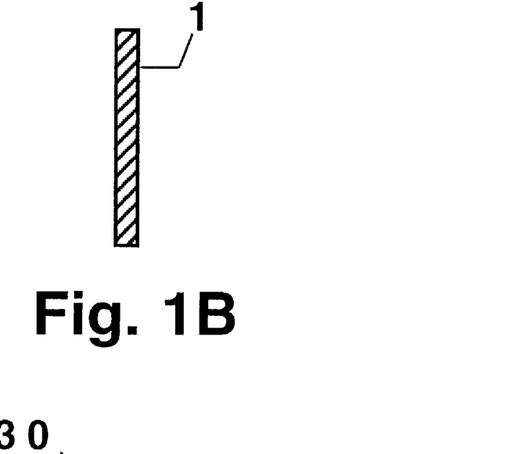
Figure 1C:
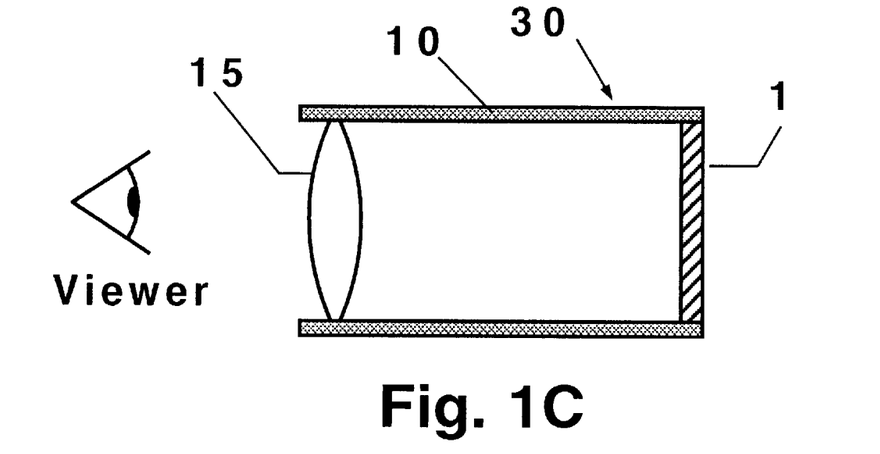
Figure 1D:
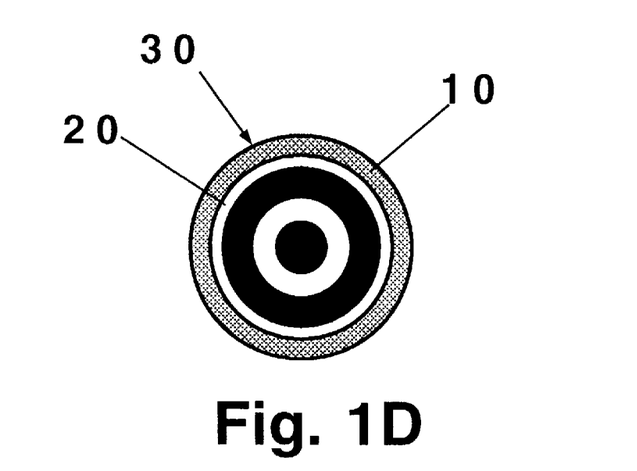

Referring to FIG. 1A there is an optical target 1 displayed with a printed pattern of a bull's-eye on its frontview. The bull's-eye pattern is printed on one side of a round typically 0.625 inch diameter translucent material with light diffusing properties such as matte acetate film or paper. Also illustrated in FIG. 1B is a side view of an optical target 1 with minimal thickness so that it transmits adequate light in ambient light conditions to sufficiently illuminate the bull's-eye pattern. In FIG. 1C a cross-sectional side view of an optical gauging assembly 30 is illustrated. Optical target 1 is mounted on one end of a 0.625 inch inside diameter opaque cylindrical housing 10 with its bull's-eye pattern facing into the cylinder. At the other end of cylindrical housing 10 is typically a 0.625 inch diameter double convex magnifying lens 15 that has a typically 10× magnification with a typically 0.5 inch field of view. The double convex magnifying lens 15 can be made of a low cost optical plastic such as acrylic. The double convex magnifying lens 15 is located in housing 10 such that the bull's-eye of optical target 1 is at the focal length of the double convex magnifying lens 15. Both the double convex magnifying lens 15 and optical target 1 can be retained within housing 10 using an adhesive or other retaining means. It can be appreciated that housing 10 could be any geometric shapes such as cyclindrical, square or rectangular tubing. A viewer would look into optical gauging assembly 30 as illustrated. In FIG. 1D a front view of optical gauging assembly 30 is illustrated. By looking through optical gauging assembly 30, the magnified image 20 of the bull's-eye of optical target 1 can be seen. The number of rings visible on image 20 is a function of the magnification and the field of view of double convex magnifying lens 15.

Figure 2A:
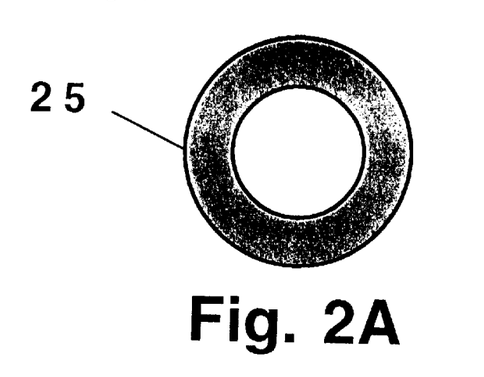
FIGS. 2A, 2B, and 2C are partial cross-sectional views of an optical gauging assembly, while it is in use, according to the invention.
Figure 2B:
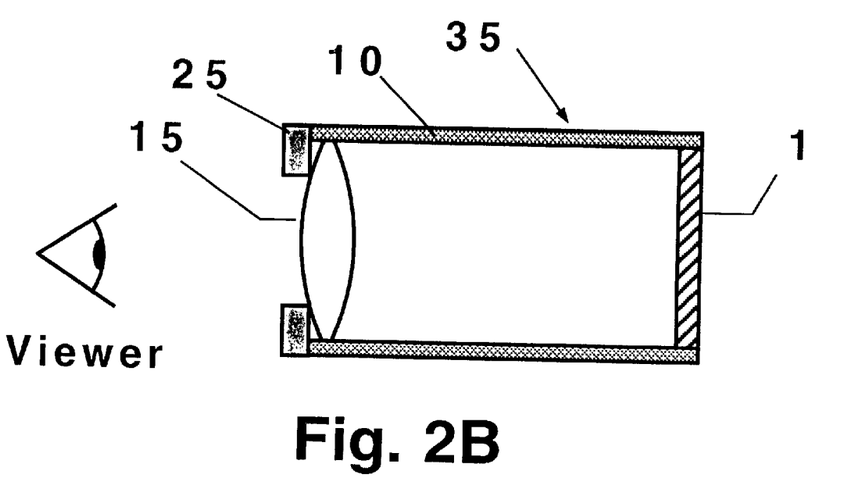
Figure 2C:
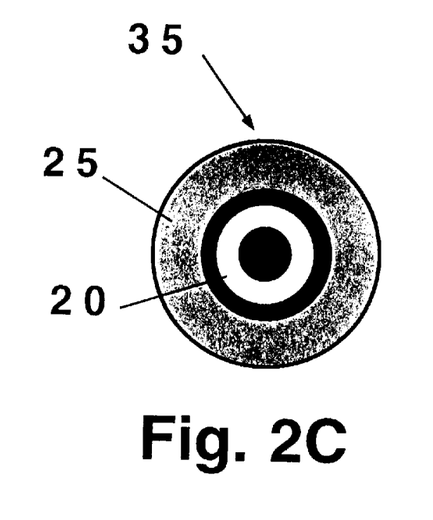

FIG. 2A illustrates a fixed aperture element 25. This aperture element has an aperature with overall diameter of typically 0.625 inches and an opening with a typically 0.5 inch diameter. Fixed aperture element 25 is made of an optically opaque material. In FIG. 2B a cross-sectional side view of optical gauging assembly 35 is illustrated. Optical gauging assembly 35 comprises all the elements of optical gauging assembly 30, FIG. 1C, with the addition of fixed aperture element 25 adjacent to the convex magnifying lens 15 as illustrated. If the opening of aperture element 25 were to be the size of a pin hole, approximately 0.06 inches then there may be no need for double convex magnifying lens 15. FIG. 2C illustrates the effect of adding fixed aperture element 25 to create optical gauging assembly 35. Fixed aperture element 25 can obstrict a portion of the Field of View as seen in image 20.

Figure 3A:
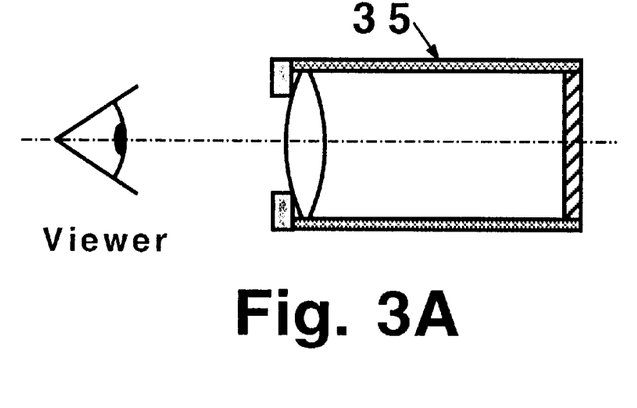
Figure 3B:
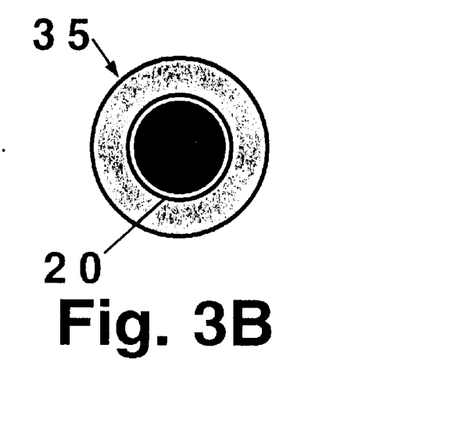
Figure 3C:
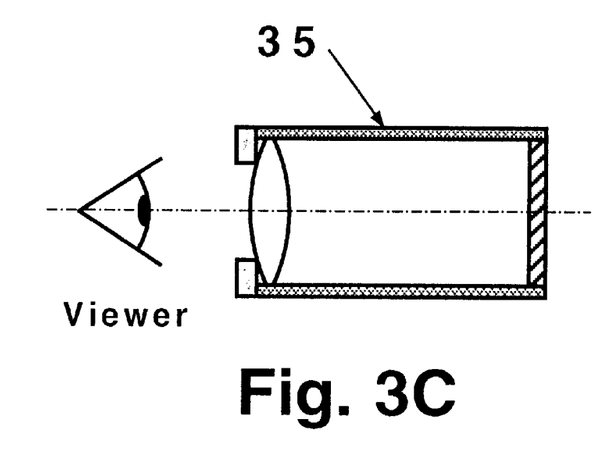
Figure 3D:
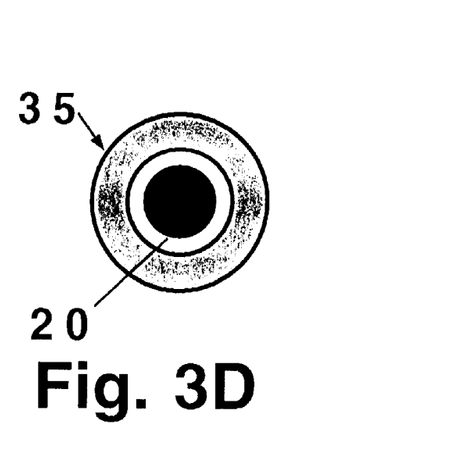
Figure 3E:
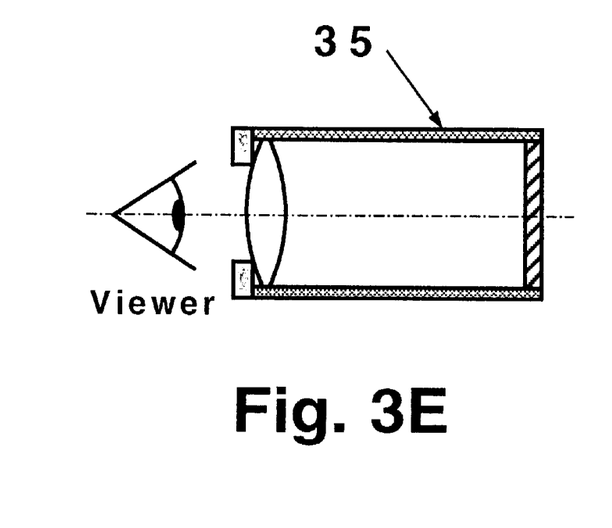

FIG. 3A, 3B, and 3C illustrate the effect on image 20 as optical gauging assembly 35 is moved along the center optical axis of the viewer as illustrated. In FIG. 3A there is a distance from the viewer where optical gauging assembly 35 yields image 20 as illustrated in FIG. 3B. The aperture element 25 and convex magnifying lens 15 produce an image 20 where the center of the bull's-eye fills the entire image 20. In FIG. 3C there is a distance from the viewer where optical gauging assembly 35 yields image 20 as illustrated in FIG. 3D. The aperture element 25 and double convex magnifying lens 15 produce an image 20 where the center and first white ring of the bull's-eye fills the entire image 20. In FIG. 3E there is a distance from the viewer where optical gauging assembly 35 yields image 20 as illustrated in FIG. 3F. The aperture element 25 and double convex magnifying lens 15 produce an image 20 where one black ring, one white ring and the center of the bull's-eye fills the entire image 20. It can be seen from FIG. 3A, 3B, and FIG. 3C that there is a direct correlation between the distance that the optical gauging assembly 35 is from the viewer and the pattern (Field of View) the viewer sees in image 20. When the viewer is given a pattern to view, the center and first white ring of the bull's-eye fills the entire image 20, then there is a fixed distance along the center optical axis of the viewer where this image occurs. This distance is repeatable independent of viewer. The distance can be calibrated by varying the pattern, aperture, or optics.

Figure 4A:
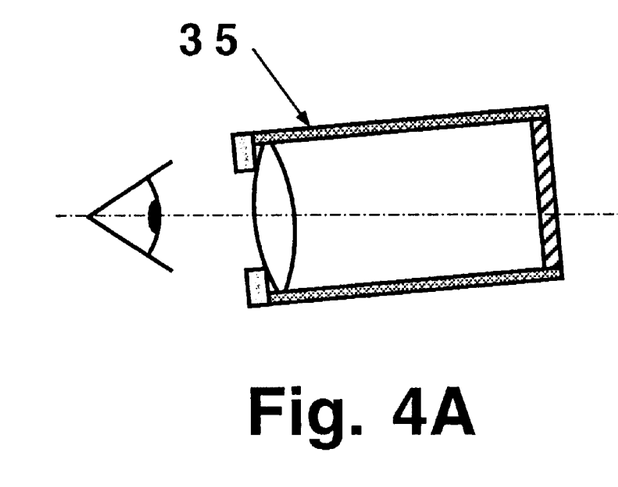
FIGS. 4A, 4B, 4C and 4D are partial cross-sectional views of an optical gauging assembly, while it is in use, according to the invention.
Figure 4B:
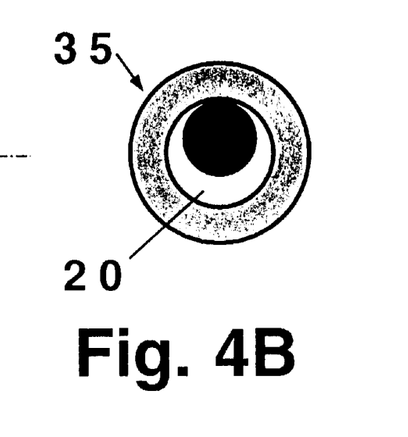
Figure 4C:
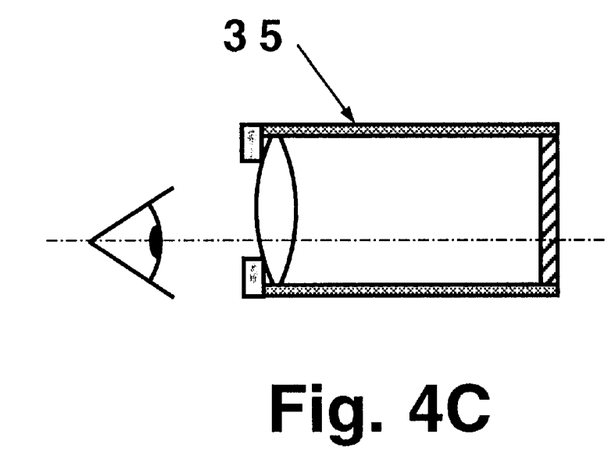
Figure 4D:
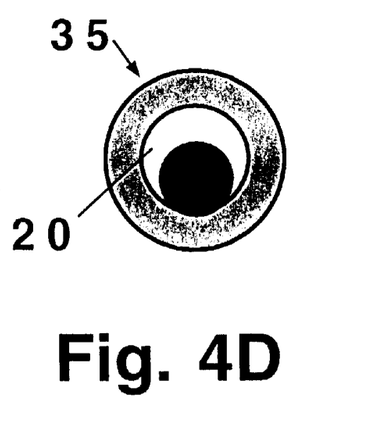
Figure 5A:
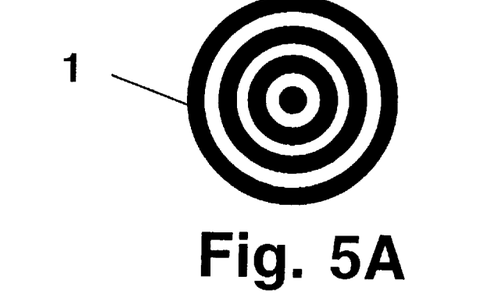
FIGS. 5A, 5B, 5C, and 5D has partial cross-sectional views of optical targets for an optical gauging assembly, according to the invention.
Figure 5B:
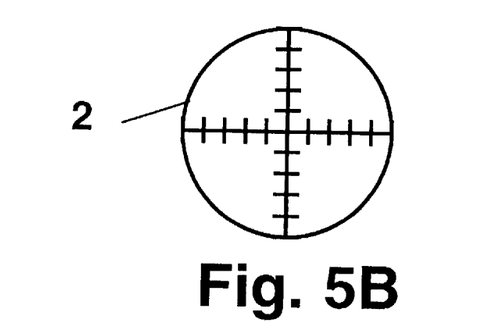
Figure 5C:
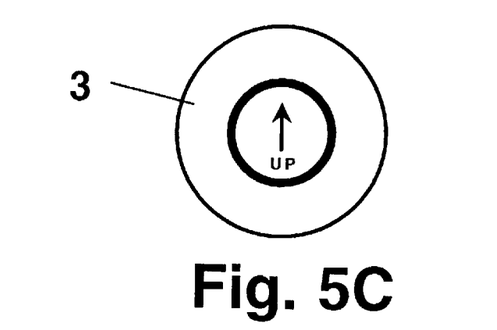
Figure 5D:
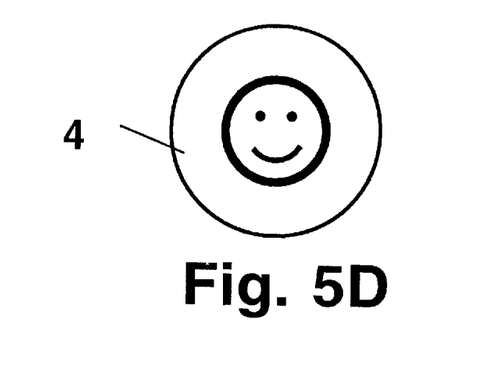

FIGS. 4A, 4B, 4C, and 4D illustrate the effect on image 20 as the optical gauging assembly 35 is rotated with respect to the center optical axis of the viewer and moved perpendicular to the center optical axis of the viewer. Using a fixed distance to the viewer similar to the distance illustrated in FIG. 3C, FIG. 4A illustrates the optical gauging assembly 35 rotated 5 degrees counterclockwise with respect to the center optical axis of the viewer. The image 20 as perceived by the viewer has the center of the bull's-eye nonconcentric and offset with respect to the center of the optical gauging assembly 35. FIG. 4C illustrates the optical gauging assembly 35 offset 25% perpendicular to the center optical axis of the viewer. The image 20 as perceived by the viewer has the center of the bull's-eye nonconcentric and offset down with respect to the center of the optical gauging assembly 35. It can be seen from FIG. 4A, FIG. 4B, 4C, and 4D that there is a direct correlation between the orientation that optical gauging assembly 35 is with respect to the center of the optical axis of the viewer and the concentricity of the image 20 that the viewer sees. Therefore optical gauging assembly 35 can be calibrated to have, a user position directly along the center of the viewers optical axis at a specific distance.

FIGS. 5A, 5B, 5C, and 5D illustrates the various patterns that can be printed and used as optical targets for the purpose of positioning optical gauging assembly 35 along the center of a viewers optical axis at a specific distance. To calibrate a fixed distance from a viewer, optical target 1, in FIG. 5A, would specify which ring of the bull's-eye to align with the outer diameter of the image 20 Field of view. To calibrate a fixed distance from a viewer, optical target 2, in FIG. 5B, would specify which vertical and horizontal hashmark to align with the outer diameter of the image 20 field of view. To calibrate a fixed distance from a viewer, optical target 3, in FIG. 5C, will align the ring with the outer diameter of the image 20 Field of view and the arrow will indicate a preferred orientation such as up. To calibrate a fixed distance from a viewer, optical target 4, in FIG. 5D, will align the ring with the outer diameter of the image 20 field of view and the graphic would specify a preferred orientation such as up. It should be apparent that the pattern can be graphically calibrated, color calibrated, or the use of text instructions or advertising can be printed within the, pattern to accomplish the same purpose.

Figure 6A:
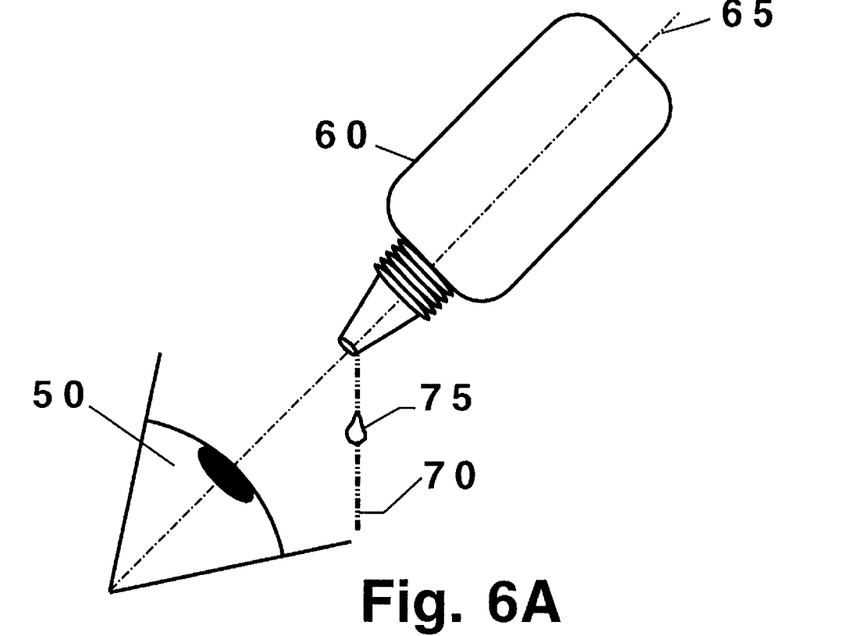
FIG. 6A is prior art of an eyedropper dispense system

FIG. 6A illustrates a problem associated with prior art means of dispensing ophthalmic drug solutions. The human eye 50 is illustrated with a 50 degree counterclockwise rotation from it normal horizontal orientation which represents its position when a human while standing is instructed to tilt his/her head as far back as possible for the purpose of dispensing ophthalmic drug solutions. The drug dispenser 60 is known art for dispensing single drops of ophthalmic drug 75 comprising a drug reservoir and dispensing means 62. The center of the human eye along optical axis 65 is where unskilled human users would position a drug dispenser 60 to dispense drops into the center of the eye. Gravity will cause the ophthalmic drug 75 to travel along path 70, and miss the eye unless drug dispenser 60 is sufficiently close to the eye. If drug dispenser 60 comes in contact with the eye the remaining ophthalmic drug solution could become contaminated. If enough drops of ophthalmic drug 75 are missed, the user may run out of ophthalmic drug solution prematurely and not get the intended full benefit of the prescribed treatment.

Figure 6B:
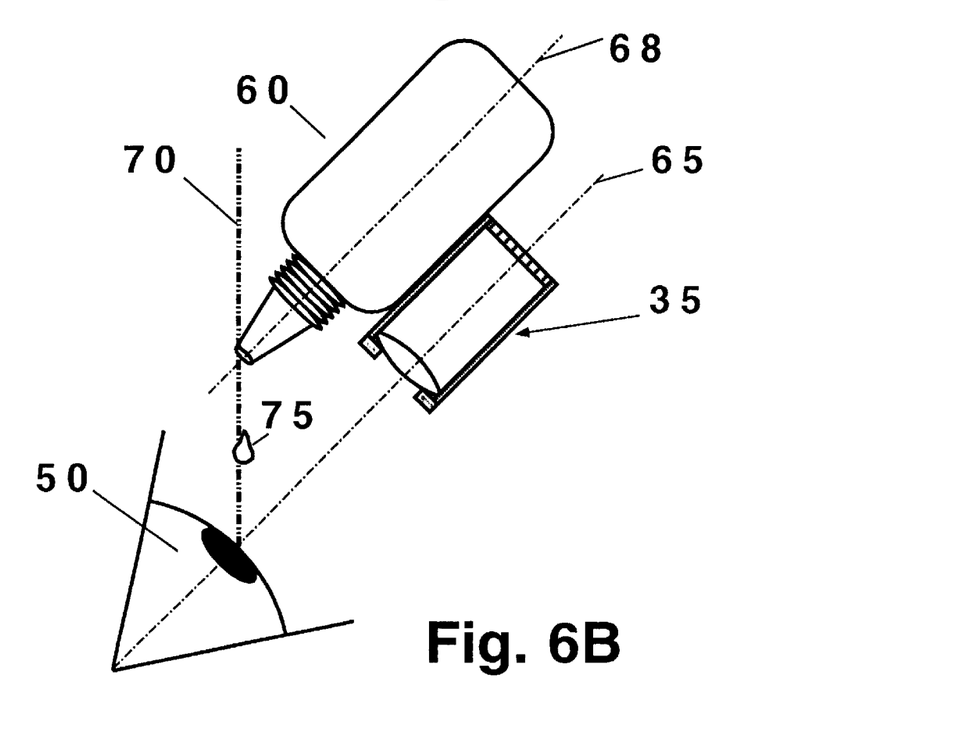
FIG. 6B is a partial cross-sectional view of an eyedropper dispense system, while it is in use, according to the invention.

FIG. 6B illustrates a preferred embodiment of the invention for dispensing ophthalmic drug solutions. The human eye 50 is illustrated with a 50 degree counterclockwise rotation from it normal horizontal orientation which represents its position when a human while standing is instructed to tilt his/her head as far back as possible for the purpose of dispensing ophthalmic drug solutions. The target for the drug dispenser 60 that the human eye 50 forms is an elliptical trace with a major axis of approximately 1 inch and a minor axis of 0.6 inches. The optical gauging assembly 35 is calibrated to be positioned at a distance illustrated along optical axis 65, approximately 1 inch from human eye 50. Drug dispenser 60 is coupled to optical gauging assembly 35 by suitable retaining means in an orientation as illustrated. The distance between optical axis 65 and center axis 68 of drug dispenser 60, approximately 0.5 inches, is calibrated and the distance from the tip of the nozzle of drug dispenser 60 and the front of optical gauging assembly 35, approximately 0.65 inches, is calibrated such that ophthalmic drug 75 follows a path 70 which intersects with the center of human eye 50. Independent of the size and shape of drug dispenser 60, as long as the dispensed point of drug dispenser 60 falls on path 70 the ophthalmic drug 75 will fall on the center of the human eye 50. The entire assembly is therefore calibrated to orient drug dispenser 60 so that ophthalmic drug 75 is always dispensed directly into the center of human eye 50. When the entire assembly is calibrated to nominal dispensing parameters, variation in angle of the human eye from user to user does not create a sufficient offset to prevent dispensing the drops on to the surface of the eye. Since optical gauging assembly 35 gives orientation and distance feedback, the distance for dispensing drops can be sufficiently far away from the surface of human eye 50 with adequate warning as to when it is too close to avoid accidental contact with human eye 50 and will therefore avoid the possibility of contamination of the remaining ophthalmic drug.

Figure 7A:
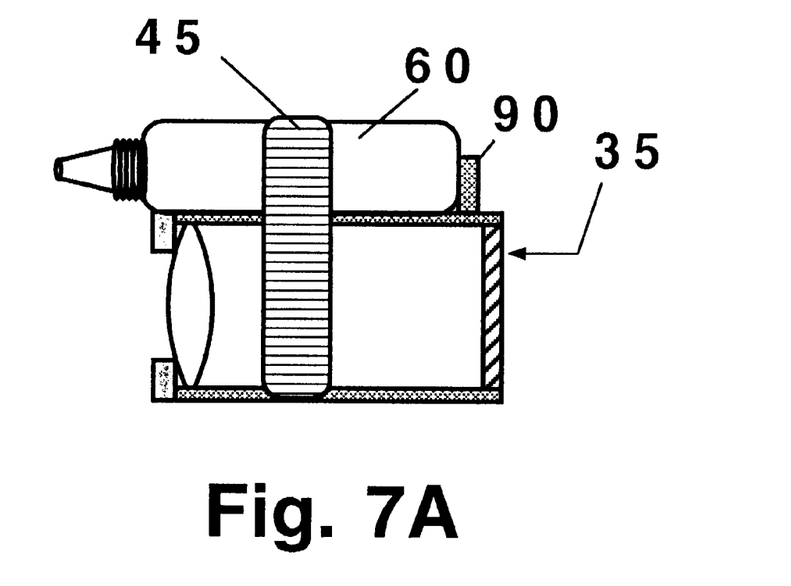
FIG. 7A is a partial cross-sectional view of an eyedropper dispense system, according to one embodiment of the invention.

FIG. 7A illustrates a preferred embodiment of the invention for dispensing ophthalmic drug solutions where the optical gauging, assembly 35 is attached by retaining means to a separate drug dispenser 60. A retaining means 45 such as adhesive tape or Velcro maintains the calibrated geometric relationship required between optical gauging assembly 35 and drug dispenser 60. There may be features such as V grooves or molded stops 90 on the optical gauging assembly 35 to help nest and retain drug dispenser 60 in its proper location. A calibration fixture not illustrated could be used to establish the proper relationship between the dispense point on drug dispenser 60 and optical gauging assembly 35.

Figure 7B:
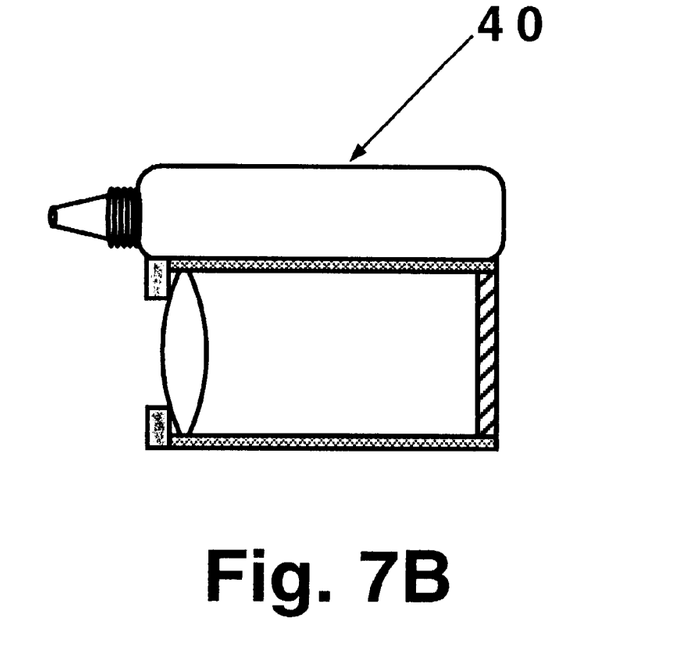
FIG. 7B is a partial cross-sectional view of an eyedropper dispense system, according to another embodiment of the invention.

FIG. 7B illustrates another preferred embodiment of the invention for dispensing ophthalmic drug solutions where all the elements of optical gauging assembly 35 and drug dispenser 60 are incorporated into a single ophthalmic drug dispenser 40. The ophthalmic drug dispenser 40 could be produced in a double shot mold where a compliant chamber for dispensing ophthalmic drugs could be molded next to a rigid plastic chamber to house the optical elements.

Figure 8:
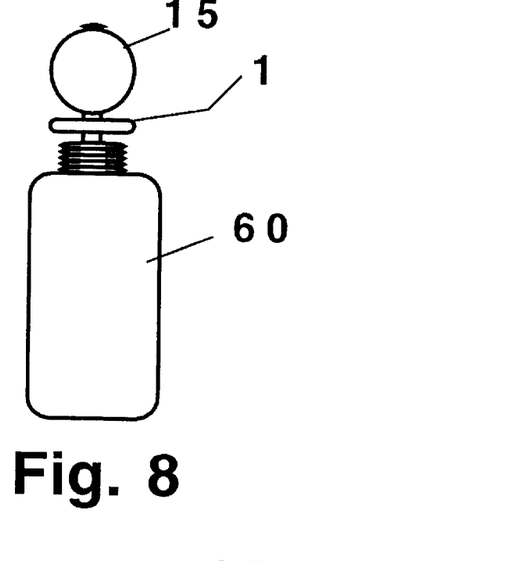
FIG. 8 is a partial cross-sectional view of an eyedropper dispense system, according to another embodiment of the invention.

FIG. 8 illustrates another embodiment of the invention for dispensing ophthalmic drug solutions where lens 15 and target 1 are coaxial with nozzle 62 of drug dispenser 60 and require no external housing.

Figure 9A:
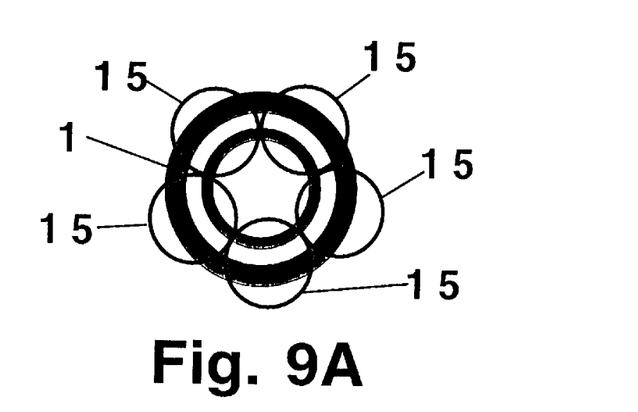
FIG. 9A and 9B are partial cross-sectional views of an eyedropper dispense system, according to another embodiment of the invention.
Figure 9B:
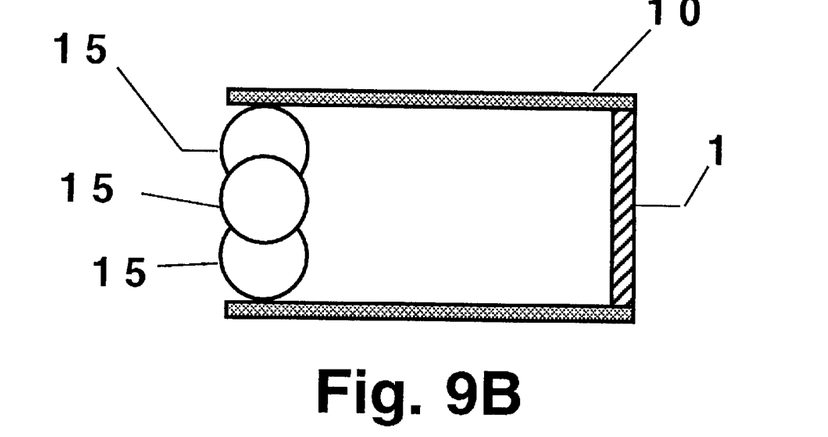

FIGS. 9A and 9B illustrates another embodiment of the invention for dispensing ophthalmic drug solutions where multiple lenses create a calibrated field of view where each lens 15 magnifies a portion of target 1. Multiple lenses can be stacked in any orientation or geometry to achieve a proper calibrated field of view.

It will thus be seen that the objects set forth above, and those made apparent from the preceding descriptions, are effectively attained and since certain changes may be made in the above construction without departing from the spirit and scope of the invention, it is intended that all matter contained in the above description or shown in the accompanying drawings, shall be interpreted as illustrative and not in a limiting sense.

It is also to be understood that the following claims are intended to cover all generic and specific features of the invention herein described and all statements of scope of the invention which as a matter of language, might be said to fall therebetween.

What is claimed is:

1. An apparatus for dispensing ophthalmic drugs; comprising:

a reservoir with dispensing means for delivering ophthalmic drugs to an eye of a user;

and optical gauging means attached to said reservoir for creating axial alignment with the user's eye and setting distance between optical gauging means and the user's eye to position said dispensing means for delivering ophthalmic drugs to user's eye;

wherein said gauging means include a viewing target having a calibrated design, and at least one lens having a field of view of proportional congruency with said design in fixed alignment with said design for viewing said design through said lens.

2. Apparatus according to claim 1, wherein said optical gauging means includes an aperture element proximal to said lens to further constrain said field of view.

3. Apparatus according to claim 1, wherein said design includes at least one circle and textual information.

4. Apparatus according to claim 1, wherein said target design includes an inner circle of a first color, and an outer circle of a second color disposed concentrically with said inner circle and wherein said field of view is circular.

5. Apparatus according to claim 1, wherein said lens is a double convex magnifying lens having a given diameter, diopter, and a field of view.

6. Apparatus according to claim 1, wherein said reservoir and said gauging means include attaching means for detachably attaching said reservoir to said gauging means.

7. Apparatus according to claim 6, wherein said attaching means provide attachment of said reservoir in a fixed relation to said gauging means.

8. Apparatus according to claim 2, including a housing for centering said aperture element, said lens and said target.

9. Apparatus according to claim 2, wherein said aperture said lens and said design are disposed coaxially with one another.

10. Apparatus according to claim 4, wherein the diameter of said field of view, of said inner circle, of focal length of said lens are selected as to provide said given relation to the users eye.

11. Apparatus according to claim 6, wherein said attaching means include at least one of hook and pile material, adhesive, snap fastener, and an elastic band.

* * * * *